US005908781A

United States Patent [19]

[11] Patent Number: 5,908,781

[45] Date of Patent: Jun. 1, 1999

Stanker et al.

[54] MONOCLONAL ANTIBODIES TO CEFTIOFUR

[75] Inventors: Larry H. Stanker, College Station, Tex.; Beate G. Rose, Chapel Hill, N.C.; John R. DeLoach, Lenoir City, Tenn.; Carol Kamps Holtzapple, College Station, Tex.

[73] Assignee: The United States of America as represented by the Secretary of Agriculture, Washington, D.C.

[21] Appl. No.: 08/766,250

[22] Filed: Dec. 10, 1996

Related U.S. Application Data

[63] Continuation of application No. 08/603,817, Feb. 20, 1996, abandoned.

[51] Int. Cl.$^{6}$ .............................. C12P 21/08; C12N 5/12

[52] U.S. Cl. .......................... 435/326; 435/7.1; 435/810; 530/388.1; 530/388.9

[58] Field of Search .............................. 435/7.1, 240.27, 435/326, 810; 530/388.9, 388.1

[56] References Cited

PUBLICATIONS

Rose et al (ACS Symposium series, 621; 82–98), 1996.
Rose et al (Bioconjugate Chem, 1995, 6:529–535).
Kohler & Milstein (Nature, 1975, 256:495–497.

Kachab et al (J. Immunol Meth, 1992, 147:33–41).

Jaglan et al (J. Assoc. Off Anal Chem, 1990, 73:26–30).

Current Protocols in Mol Bio, Ausubel et al, Eds, Green Pub Assoc & Wiley Interscience, 1992, pp. 11,15,2–4.

Harlow & Lane (Antibodies, Cold Spring Harbor Lab, 1988, p. 141).

Rose et al (J. Agri. Food Chem, 1992, 44: 622–627.

*Primary Examiner*—Lila Feisee
*Assistant Examiner*—Susan Ungar
*Attorney, Agent, or Firm*—Randall E. Deck; M. Howard Silverstein; John D. Fado

[57] ABSTRACT

Hybridoma cell lines have been generated which produce and secrete monoclonal antibodies which selectively bind to the ceftiofur. These hybridomas may be obtained by using as an immunization agent or immunogen, desfuroyl ceftiofur which has been conjugated to an immunogenic carrier. Ceftiofur in biological samples may be detected and quantified by contacting the sample with the antibodies to form a ceftiofur/antibody immunocomplex when ceftiofur is present, which immunocomplex may then be detected. The monoclonal antibodies may also be incorporated into kits for the detection and quantification of ceftiofur.

9 Claims, No Drawings

MONOCLONAL ANTIBODIES TO CEFTIOFUR

CROSS-REFERENCED TO RELATED APPLICATIONS

This application is a continuation of application Ser. No. 08/603,817, filed Feb. 20, 1996, now abandoned, the contents of which are incorporated herein.

BACKGROUND OF THE INVENTION

1. Field of the Invention

This invention relates to hybridoma cell lines and monoclonal antibodies produced therefrom which may be used to detect ceftiofur.

2. Description of the Prior Art

Ceftiofur is a broad-spectrum, β-lactamase-resistant cephalosporin which exhibits excellent antimicrobial activity by virtue of its 2-(2-aminothiazol-4-yl)-2-methoxyaminoacetamide substituent at the C-7 position of the cephem nucleus (Labeeuw and Sahli, U.S. Pat. No. 4,464,367; Yancey et al., 1987, *Am. J. Vet. Res.*, 48:1050–1053). Ceftiofur has been approved by the FDA and is used for the treatment of respiratory diseases in cattle and horses (Food and Drug Administration, 1988, *Fed. Regist.*, 53:5369–5370; and 1991, *Fed. Regist.*, 56:119).

Current detection methods for cephalosporins include HPLC procedures (Rouan, 1985, *J. Chromatogr.* 340:361–400) and biological assays (Wise et al., 1980, *Antimicrob. Agents Chemother.*, 17:84–86). Recent HPLC methods for ceftiofur can detect 0.5 ppm ceftiofur equivalents (Jaglan et al., 1990, *J. Assoc. Off. Anal. Chem.*, 73:26–30; Gilbertson et al., 1990, *J. Agric. Food Chem.*, 38:890–894). Other methods for the detection of ceftiofur which have been described include agar gel diffusion (Cervantes et al., 1993, *Am. J. Vet. Res.*, 53:573–575. Owens et al., 1990, *J. Dairy Sci.*, 73:3449–3456), "DELVOTEST-P", which is a calorimetric bacterial inhibition test (Jaglan et al., 1992, *J. Dairy Sci.*, 75:1870–1876. Owens et al., 1990, ibid), the *Bacillus stearothermophilus* disk assay, the Charm test II, which is a receptor-binding assay (Jaglan et al., 1992, ibid), and a cylinder-plate microbiological assay (Jaglan et al., 1992, ibid; Gilbertson et al., 1990, ibid). Unfortunately, these tests require labour-intensive sample preparations, lengthy data acquisition times, and in some cases costly and sophisticated equipment.

A commercial immunoassay for ceftiofur is currently available (Idetek Inc., Sunnyvale, Calif.). However, the assay is based upon a polyclonal antibody for ceftiofur rather than a monoclonal antibody.

SUMMARY OF THE INVENTION

We have now discovered hybridoma cell lines which produce and secrete monoclonal antibodies which selectively bind to ceftiofur. We have unexpectedly found that these hybridomas may be obtained by using as an immunization agent or immunogen, desfuroyl ceftiofur which has been conjugated to an immunogenic carrier. Ceftiofur in biological samples may be detected and quantified by contacting the sample with the antibodies to form a ceftiofur/antibody immunocomplex when ceftiofur is present, which immunocomplex may then be detected. The monoclonal antibodies may also be incorporated into kits for the detection and quantification of ceftiofur.

It is an object of this invention to provide hybridoma cell lines that produce and secrete high affinity monoclonal antibodies which selectively bind to ceftiofur.

Another object of this invention is to provide immunoassay methods for the measurement of ceftiofur in biological samples.

A further object is to provide kits useful for the assay of ceftiofur which include the monoclonal antibodies described herein.

Yet another object is to provide an immunization agent which may be used to produce hybridoma cell lines that produce and secrete high affinity monoclonal antibodies which selectively bind to ceftiofur.

Other objects and advantages of this invention will become readily apparent from the ensuing description.

DETAILED DESCRIPTION OF THE INVENTION

In accordance with this invention, we have created hybridoma cell lines that produce monoclonal antibodies which selectively bind ceftiofur (free or conjugated to a protein) and its monosodium salt, ceftiofur sodium. We have unexpectedly discovered that by use of a novel immunogen, monoclonal antibodies may be produced which possess improved specificity and increased affinity for ceftiofur. The antibodies of this invention may be used to rapidly and accurately detect and quantify ceftiofur, providing an indicator of the level of this compound in biological samples. In addition, we have also discovered that these antibodies may also selectively bind to and be used to detect desfuroyl ceftiofur and closely related cephalosporins such as cefotaxime, cefteram, and ceftriaxone.

Traditionally, preparation of hybridomas may be accomplished using conventional techniques such as described by Kohler and Milstein [Nature, 256:495–497 (1975)], Koprowski et al. [U.S. Pat. No. 4,196,265], Wands [U.S. Pat. No. 4,271,145], or Stanker et al. [U.S. patent application Ser. No. 08/081,591, filed Jun. 23, 1993], the contents of each of which are incorporated by reference herein. Briefly, the process of preparation comprises the steps of immunizing an animal with the antigen of interest, recovering splenocytes or lymphocytes from the animal, fusing the splenocytes or lymphocytes with continuously replicating myeloma cells to produce hybrid cells, and screening the resultant hybrid cells for the production of antibodies to the antigen.

Often, the compound of interest is a relatively small molecule, and hence is itself incapable or only poorly capable of stimulating the immune system to produce antibodies. To render such compounds immunogenic, they are generally conjugated to an immunogenic carrier in such a manner that the resultant immunogen is capable of stimulating the immune system of an animal to produce specific antibodies that are capable of binding the unconjugated compound. Application of this traditional protocol for the generation of monoclonal antibodies to a small compound such as ceftiofur, would logically dictate an immunogen prepared by conjugation of ceftiofur to a carrier protein. However, in a departure from established practice, we describe here the preparation of monoclonal antibodies using significantly different, novel immunogens.

The method of preparing the hybridomas comprises the following steps:

Immunogen. The immunization agent of this invention is not constructed from ceftiofur per se, but from its corresponding hydrolyzed form, desfuroyl ceftiofur. Unlike ceftiofur, desfuroyl ceftiofur used herein lacks a furanyl thio ester ring component, possessing in its place a free thiol group. The structures of ceftiofur and desfuroyl ceftiofur are shown in formulas I and II, respectively:

(I)

(II)

The hapten desfuroyl ceftiofur may be prepared by acid or base catalyzed hydrolysis of the thioester bond of ceftiofur using techniques conventional in the art. Upon hydrolysis, the furoic acid group of ceftiofur is cleaved, leaving desfuroyl ceftiofur having a free thiol group. A detailed description of the preferred method for preparation of desfuroyl ceftiofur is provided in Example 1 hereinbelow.

The immunization agent is prepared by covalently conjugating an immunogenic carrier to desfuroyl ceftiofur. Immunogenic carriers are defined herein as any compound to which the haptens may be attached to render them immunogenic. Suitable carriers are well known and may be readily determined by the practitioner skilled in the art. Without being limited thereto, preferred carriers include proteins such as keyhole limpet hemocyanin (KLH), bovine serum albumin (BSA), ovalbumin and human thyroglobulin.

The immunogenic carrier may be conjugated to the desfuroyl ceftiofur molecule directly or through an optional crosslinking agent or spacer. In accordance with the preferred embodiment, the immunogen is created by conjugation of a carrier protein to the free thiol group of desfuroyl ceftiofur. As described in greater detail in Example 1, in a particularly preferred embodiment, desfuroyl ceftiofur is conjugated to a carrier protein modified by reaction with a sulfhydryl reactive bifunctional crosslinking agent, such as succinimidyl-4-(N-maleimidomethyl)cyclohexane-1-carboxylate (SMCC) or sulfo-SMCC (s-SMCC), either of which form a maleimide-activated carrier protein. Other crosslinking agents suitable for conjugating a carrier protein and desfuroyl ceftiofur through the hapten's thiol group, include but are not limited to the organic solvent soluble agents Succinimidyl 4-(p- maleimidophenyl)-butyrate (SMB), N-[($\gamma$-Maleimidobutyryl)oxy]succinimide ester (GMBS), N-Succinimidyl[4-iodoacetyl]-aminobenzoate (SIAB), and m-Maleimidobenzyl-N-hydroxysuccinimide ester (MBS), or their corresponding water soluble sulfonated forms sulfo-SMPB (s-SMPB), sulfo-GMBS (sGMS), sulfo-SIAB (s-SIAB), and sulfo-MBS (s-MBS). Immunogens prepared by conjugation of desfuroyl ceftiofur to a carrier protein through a crosslinking agent may be generally described by the formula (III):

(III)

wherein L refers to the optional crosslinking agent and R is a carrier protein.

Immunization. To generate antibody-producing splenocytes or lymphocytes, an immunizing preparation comprising the desfuroyl ceftiofur-carrier complex is injected into an immunologically competent animal. The preparation may also contain other proteins, although pure or partially pure compositions of the conjugate in a pharmaceutically acceptable carrier are preferred.

Without being limited thereto, rats and particularly mice are preferred animals for immunization because of ease of handling. Preparation of hybridomas using splenocytes from these animals fused to a variety of myeloma cell lines have been reported by many investigators.

Inoculations of the animal can be by various routes. A series of three inoculations, generally at two week intervals, with a composition of the complex in isotonic saline with RIBI adjuvant (Immunochem Research, Inc., Hamilton, Mont.) elicits good antibody response, and is preferred. The skilled practitioner will recognize that other routes of administration, immunization schedules, and carriers or adjuvants may be used.

Hybridization. Splenocytes or lymphocytes recovered from the immunized animal are fused with continuously replicating tumor cells, such as myeloma or lymphoma cells, cultured, and hybridoma cells selected. Many continuously replicating tumor cell lines are available which may be used as fusion partners with the splenocytes. Without being limited thereto, preferred myeloma cells include P3-NS1-K653, and particularly SP2/0.

Fusion and culture of the cells can be performed using conventional techniques. In accordance with one well-known effective procedure, the splenocytes and myeloma cells are fused by exposure to polyethylene glycol. Hybrid cells are selected by culture in hypoxanthine-aminopterin-thymidine (HAT) medium, whereby unfused myeloma cells are killed by HAT and splenocytes die out, leaving only the hybrid cells. The resultant hybridomas are then grown in HAT or other suitable culture medium and assayed for antibody production.

Screening. Samples of the supernatant culture fluid from the hybridomas are screened for antibodies to ceftiofur or closely related analogs. While the supernatants may be screened using a plurality of well-known techniques such as RIA, FIA and ELISA, in accordance with the preferred embodiment, a modification of the direct-binding ELISA (db-ELISA) is employed. Generally, solid substrates, such as beads or the wells of a microtiter plate, which are coated with ceftiofur-or desfuroyl ceftiofur-carrier complex, are used to bind anti-ceftiofur antibody in the supernatants, and bound antibody is then detected. Detection of bound antibody may be accomplished by addition of enzyme-labeled anti-immunoglobulin antibodies followed by enzyme substrate. Horse radish peroxidase and its substrate, 2,2'-azinobis-3-ethylbenthiazolinesulfonic acid (ABTS) are preferred enzyme/substrate labels. However, it is understood that other enzyme/substrate labels or non-enzyme labels such as radiolabels or chromophores may also be used.

Cloning. Cloning of hybridomas which are positive for desired antibody production can be carried out as soon as they are detected by any method known in the art. Hybridomas having a positive response in the ELISA screen are preferably expanded and subcloned one or more times by limiting dilution to assure monoclonality.

The supernatant culture fluid from the cloned hybridomas may also be screened to select for those producing antibodies having a high affinity for ceftiofur. Affinity may be measured using a variety of well known techniques, such as ELISA, RIA or equilibrium dialysis using labeled ceftiofur. In the preferred embodiment, affinity is measured by competitive indirect ELISA as described in Example 2, and is conducted at a final antibody concentration (dilution from the tissue culture supernatant) to give 50% of maximal binding to a ceftiofur coated substrate or assay well (i.e., the concentration of the antibody that results in 50% of the plateau activity in direct binding ELISA). In accordance with this embodiment, the antibody containing supernatant is added to a ceftiofur or ceftiofur-complex coated substrate such as the wells of a microtiter plate, together with a range of concentrations of free ceftiofur as a competitor. Following incubation and washing, bound antibody in the wells is determined in the same manner as the db-ELISA. Percent inhibition may be calculated as $(1-B/B_o)\times100$, where B is the optical density (OD) of a well with a competitor and $B_o$ is the mean OD of the wells without competitor (control). The relative affinity of the antibodies may be accurately measured as the concentration of free ceftiofur added to the wells that results in at least 20% inhibition ($IC_{20}$) of control activity. However, for greater accuracy, the affinity may be alternatively measured at 50% inhibition ($IC_{50}$).

Generally, ceftiofur or ceftiofur-carrier complex will be used in this screening process. However, when antibodies having broader range of specificity are desired, the hybridomas may also be screened for production of antibodies effective for binding analogs of ceftiofur, particularly desfuroyl ceftiofur or those cephalosporins containing the cephem nucleus, the thiazolyl ring, and the methoxyiminoacetamide oxime, such as cefotaxime, cefteram, and ceftriaxone.

Once hybridomas producing and secreting the desired anti-ceftiofur antibodies are identified, large quantities of the antibodies may be produced in tissue culture using well-known techniques. Alternatively, antibodies may be produced within host animals, such as by ascites formation in syngenic mice. Monoclonal antibodies so produced may be purified, for example, by affinity chromatography on a protein A or G resin, or using ceftiofur bound to a resin.

The monoclonal antibodies produced in accordance with this invention possess high affinity for ceftiofur, allowing the rapid determination of this antibiotic at low levels. As shown in Table 1 and described in detail in Example 2, when the sensitivity was measured at a high standard of accuracy ($IC_{50}$) by competitive inhibition ELISA, the detection limits of the antibodies for ceftiofur ranged from 0.33 to 32 ppb (using 100 $\mu$l samples added to microtiter plate wells). Furthermore, the monoclonal antibodies of this invention may also selectively bind to desfuroyl ceftiofur and closely related cephalosporin analogs which contain all of the cephem nucleus, the thiazolyl ring, and the methoxyiminoacetamide oxime. Without being limited thereto, compounds which may be detected include one or more of ceftiofur, desfuroyl ceftiofur, and the cephalosporin analogs cefotaxime, cefteram, and ceftriaxone.

The antibodies may be used to detect and/or quantify these compounds, and particularly ceftiofur, in unknown samples using a variety of conventional immunosorbent assays including but not limited to RIA, FIA or ELISA. Although the assays are described hereinbelow for the determination of ceftiofur, it is understood that determination of the above-mentioned compounds may be conducted by substitution of ceftiofur with the appropriate antigen of interest. A competitive inhibition ELISA similar to that used to screen the hybridomas is preferred. In this assay, a sample to be analyzed is incubated with the monoclonal antibody for ceftiofur and a solid substrate coated with ceftiofur or ceftiofur-carrier complex. After incubation, the solid phase is drained and washed, and bound antibody on the substrate is detected and percent inhibition calculated as described earlier. The concentration of ceftiofur in the sample may then be determined by reference to a standard curve constructed from assays using known levels of ceftiofur.

In one alternative embodiment, ceftiofur may be determined by a competition ELISA such as described in Brandon et al. (U.S. Pat. No. 5,053,327, the contents of which are incorporated by reference herein) using the monoclonal antibody of the invention attached to a solid support. For example, the anti-ceftiofur antibody may be immobilized on a solid support such as a bead or microtiter well. The unknown sample to be analyzed (or analytical standards of ceftiofur) are then added with enzyme or radiolabeled ceftiofur, and the amount of labeled ceftiofur bound to the antibody is measured, using a substrate when the label is an enzyme. The amount of ceftiofur in the sample is inversely proportional to the amount of bound labeled ceftiofur. In another alternative, the monoclonal antibody may be attached to a solid support for use in conventional double-antibody sandwich ELISA procedures.

With any of the above-described assay formats, the monoclonal antibodies of the invention may be incorporated into kits, alone or preferably together with any other necessary reagents. A preferred kit for use herein comprises a first container including the monoclonal antibody, a second container including detection means effective for detecting bound antibody, and a solid phase support having ceftiofur attached thereto.

Determination of ceftiofur in a variety of biological samples, including animal tissue, dairy products, and animal fluids such as serum, may be conducted using the above-described assays with minimal sample preparation and using simple extraction procedures. In one embodiment, ceftiofur may be detected in milk at a few ppm without any clean up. For the analysis of tissue samples, the tissue may be homogenized in buffer, such as Tris-HCl, centrifuged, and the liquid phase recovered and used directly in the immunoassay. Although any animal tissue may be analyzed, the assay is particularly valuable for the determination of ceftiofur in meats. Tissue for analysis in accordance with the invention may originate from virtually any animal. Without being limited thereto, the assays are preferably used for the analysis of tissue samples and meats from domestic animals, particularly bovine, swine, and poultry.

Another application of the monoclonal antibodies is affinity purification of ceftiofur. The antibodies may be bound to a matrix, column, or other support using well-known techniques and used to recover or remove ceftiofur from any desired material. Alternatively, the monoclonal antibodies may be incorporated into sensors such as solid phase electronic devices for detection of ceftiofur in sample materials.

The following examples are intended only to further illustrate the invention and are not intended to limit the scope of the invention which is defined by the claims.

EXAMPLES

The preparation of the immunogen for use in the production of the hybridomas, and the assays (both ELISA and competitive indirect ELISA) in the following Examples, are described in Rose et al. (1995, Bioconjugate Chemistry, 6(5):529–535), the contents of which are incorporated by reference herein.

Example 1

Immunogen Production

Hapten-Protein Conjugates. Two conjugation methods were used to prepare hapten-protein conjugates as described earlier (Rose et al., 1995).

Carrier proteins. Bovine serum albumin (BSA) and ovalbumin (OVA) (both obtained from Pierce, Rockford, Ill. were thiolated using 2-iminothiolane hydrochloride (Traut's reagent). Typically, 66 mg BSA or 44 mg OVA in 2.2 mL dilute phosphate buffered saline, PBS-A (0.05M sodium phosphate, 0.075M sodium chloride, 0.1M EDTA in deionized water, pH 7.2), and a 3× molar excess of Traut's reagent dissolved in 20 μL of the same buffer were added together. The resulting mixtures were stirred overnight at ambient temperature. The thiolated BSA (BSA-SH) and thiolated OVA (OVA-SH) were dialyzed for several days against PBS-A. The maleimide-activated BSA (BSA-SMCC) and KLH (KLH-SMCC)(both obtained from Pierce, Rockford, Ill.) were activated by the manufacturer using the cross-linking reagent sulfo-succinimidyl-4-(N-maleimidomethyl) cyclohexane-1-carboxylate (s-SMCC).

Hapten-Protein Conjugates. Ceftiofur was conjugated to BSA, OVA, BSA-SMCC, and KLH-SMCC by the following procedures:

Preparation of Ceftiofur-SMPB Conjugates. Ceftiofur sodium (82 mg)(The Upjohn Co., Kalamazoo, Mich.) was dissolved in 500 μL PBS-A, and 10 mg sulfosuccinimidyl 4-(p-maleimidophenyl)-butyrate (s-SMPB)(Pierce, Rockford, Ill.) in 20 μL DMF was added. The resulting mixture was stirred for 10–15 min, added dropwise to 30 mg BSA-SH (1.5 mL of a 20 mg/mL stock solution), stirred overnight at ambient temperature, and then dialyzed exhaustively against PBS-A. Similarly, 52 mg ceftiofur sodium in PBS-A and 5 mg s-SMPB in 20 μL N,N-dimethylformamide (DMF) were added dropwise to 20 mg of OVA-SH (1 mL of a 20 mg/mL stock solution), and the mixture was stirred overnight at ambient temperature and dialyzed exhaustively against PBS-B (0.05M sodium phosphate, 0.075M sodium chloride in deionized water, pH 7.2). These conjugates were abbreviated as BSA-S-SMPB-Cef and OVA-S-SMPB-Cef, respectively.

Preparation of Ceftiofur-GMBS Conjugates. Ceftiofur-GMBS conjugates were prepared as described above except that s-SMPB was replaced with N-[(γ-maleimidobutyryl) oxy]sulfosuccinimide ester (s-GMBS)(Pierce, Rockford, Ill.). These conjugates were abbreviated as BSA-S-GMBS-Cef and OVA-S-GMBS-Cef, respectively. In this conjugation the free amine on ceftiofur reacts with the succinimide moiety of the heterobifunctional cross-linking reagent, s-GMBS. The maleimide moiety of the hapten-cross-linker is coupled to sulfhydryl groups on thiolated carrier proteins.

Preparation of desfuroyl Ceftiofur and desfuroyl Ceftiofur-SMCC Conjugates. Briefly, ceftiofur was hydrolyzed to produce the desfuroyl ceftiofur metabolite in situ. The hydrolysis of ceftiofur was followed with slight modification according to the literature (Chapman and Owen (1950, Dithiols part IV, J. Chem. Soc. London, pp. 579–585, the contents of which are incorporated by reference herein). Potassium carbonate (30 mg) was dissolved in PBS-A (100 μL) and added to a solution of ceftiofur sodium (50 mg) in methanol (1 mL) and DMF (40 μL). The reaction mixture was stirred overnight under an argon atmosphere to ensure complete hydrolysis of the furan ring. The presence of the thiol was checked by TLC in $CHCl_3$-MeOH (1:1) and spots were visualized by development of the TLC in iodine according to the method of Brown and Edwards (1968, J. Chromatogr., 38:543). Evaporated solvents were replenished by addition of 500 μL PBS-A. Following this, 1.5N HCl was added to adjust the pH to 7. The solution containing the desfuroyl ceftiofur was then added dropwise to 1 mL BSA-SMCC (5 mg/mL stock solution in deionized water) or 1 mL KLH-SMCC (5 mg/mL stock solution in deionized water), stirred overnight in the cold and subsequently dialyzed against PBS-A and PBS-B, respectively. The free thiol reacts immediately with the maleimide portion of the heterobifunctional cross-linking agent s-SMCC. These conjugates were abbreviated as BSA-SMCC-desCef and KLH-SMCC-desCef, respectively, and have the structure shown in formula (IV):

(IV)

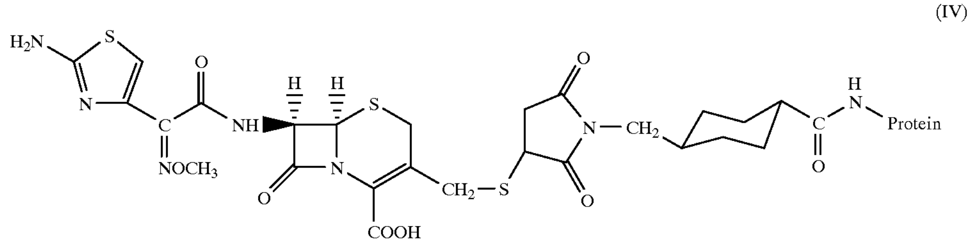

All hapten-carrier protein conjugates were analyzed by nondenaturing gel electrophoresis as described by Kamps-Holtzapple et al. (1993, J. Immunol. Methods, 164:245–253, the contents of which are incorporated by reference herein).

KLH-SMCC-desCef was used as the immunogen and BSA-SMCC-desCef was used as the plate-coating antigen in initial screening experiments described in Example 2, hereinbelow. The evaluation of the ciELISA's was performed using a heterologous plate-coating antigen, BSA-S-GMBS-Cef, instead of BSA-SMCC-desCef, as described earlier (Rose et al., 1995).

Example 2

Hybridoma Production

Immunization Protocol. Female Balb/c mice (Harlan-Sprague-Dawley, Houston, Tex.) were immunized intraperitoneally on day 1 with 100 $\mu$g of KLH-SMCC-desCef in a 0.2 mL solution of physiological saline and RIBI adjuvant (prepared as suggested by the manufacturer, RIBI ImmunoChem Research, Inc., Hamilton, Mont.), and boosters were given on days 14, 28, and 43. Mice were bled through the tail vein on day 50 and serum titers were determined by ELISA using BSA-S-GMBS-Cef as the plate-coating antigen. On day 145, one mouse was boosted with a 100 $\mu$g dose of the immunogen prepared in physiological saline (no RIBI adjuvant) and 4 days later its spleen was removed and used for the production of hybridomas.

Hybridoma Production. Hybridomas were produced following fusion of SP2/0 myeloma cells with splenocytes from immunized mice as previously described (Stanker et al., 1986, J. Immunol., 136:615–622, the contents of which are incorporated by reference herein). The fused cells were resuspended in hypoxanthine-aminopterin-thymidine (HAT) medium and plated onto 30 macrophage-containing 96-well microculture plates and were incubated at 37° C. in a 5% $CO_2$ atmosphere, and subsequently supernatants were screened for antibodies against ceftiofur by the indirect ELISA method at 10 days following the fusion. Hybridoma cells that produced monoclonal antibodies capable of being inhibited by ceftiofur were cloned at least twice by limiting dilution.

Antibodies and ELISA Methods. A standard indirect ELISA method in which the hapten conjugate is immobilized on 96-well microtiter plates was used to evaluate the response of Balb/c mice towards the immunogen KLH-SMCC-desCef. The microtiter immunoplates (PGC Scientifics, Gaithersburg, Md.) were washed three times with a solution of 0.05% (v/v) polyoxyethylene sorbitan monolaurate (TWEEN 20)(Sigma Chemical Co., St. Louis, Mo.) in deionized water (TWEEN 20-water) and then coated with 100 $\mu$L of the coating antigen, BSA-SMCC-desCef (100 ng/well) in deionized water. The plates were dried overnight at 37° C. The plates were then washed three times with PBS-9 (0.01M sodium phosphate, 0.15M sodium chloride, pH 9) and the unbound active sites were blocked with 200 $\mu$L of 3% (w/v) nonfat milk in PBS-9 for 30 min at 37° C. The plates were washed three times with PBS-9, and 100 $\mu$L of supernatant containing the antibody was added to the microtiter plates, which were subsequently incubated for 60 min at 37° C. The unbound antibody was removed by washing the plate five times with TWEEN 20-water. Next, 50 $\mu$L of goat anti-mouse IgG-peroxidase conjugate (1:500 dilution)(Sigma Chemical Co., St. Louis, Mo.) was added, followed by incubation of the plates at 37° C. for 60 min. Finally, the plates were washed five times with TWEEN 20-water, 100 $\mu$L of K-blue substrate (Elisa Technologies, Lexington, Ky.) was added, and the absorbance was read at 655 nm.

Ten days following cell fusion, 3-5 hybridoma colonies were observed in 90–95% of the wells of each 96-well plate. Positive results (greater than twice that of the background) were observed with the supernatants from 144 wells in the initial screening ELISA. The cells in these were expanded and analyzed by competitive indirect ELISA (ciELISA) as described below for inhibition of antibody binding in the presence of free (unconjugated) ceftiofur on BSA-S-GMBS-Cef-coated antigen plates.

For the ciELISA, the plates were prepared as above except that BSA-S-GMBS-Cef was used as the plate-coating antigen. Competitors were prepared in assay buffer (0.1M Tris, 0.15M sodium chloride, 0.01% (w/v) nonfat milk in deionized water, pH 7.75), added to the wells, and diluted in a 2-fold fashion immediately prior to addition of the anti-ceftiofur monoclonal antibody (Mab). Tissue culture media containing the anticeftiofur MAbs were used at a final dilution of 1:20 and 1:100 (for MAbs Cef-68 and Cef-116, respectively). The following competitors were used in a cross-reactivity study: ceftiofur sodium, cefteram sodium (Hoffmann-La Roche Inc., Nutley, N.J.), ceftriaxone sodium (Hoffmann-La Roche), cefuroxime sodium (Glaxo Man. Serv. Ltd., Barnard Castle, County Durham, England), ceftazidime pentahydrate (Glaxo), amoxicillin, ampicillin sodium, cefaclor, cefadroxil, cefamandole sodium, cefazolin sodium, cefoperazone sodium, cefotaxime sodium, cefoxitin sodium, cefsulodin sodium, cephalothin sodium, cephapirin sodium, cephradine, cloxacillin sodium, and penicillin-G sodium. Except where indicated otherwise, competitors were obtained from Sigma Chemical Co. (St. Louis, Mo.). The competitors were diluted to afford a solution containing a concentration range of 100–1000 ng/well in column 2 of the 96-well microtiter plates. Each competitor was serially diluted across the plate with columns 11 and 12 serving as controls (i.e. no competitor).

Ten of the original 144 cell cultures were observed to produce antibodies whose binding were inhibitable by ceftiofur. Cells from these ten hybridomas were subcloned resulting in the establishment of two stable monoclonal cell lines secreting anticeftiofur antibodies. These cell lines were designated as Cef-68 and Cef-116.

Cell line Cef-116 has been deposited under the Budapest Treaty in the American Type Culture Collection (10801 University Blvd., Manassas, Va. USA) on Aug. 31, 1998, and has been assigned accession number ATCC HB-12562.

Antibody Characterization. The ability of Cef-68 and Cef-116 to recognize free (unconjugated) ceftiofur was evaluated using the ciELISA. The fifty percent inhibition of control activity ($IC_{50}$) was observed at 32 ppb for Cef-68. MAb Cef-116 was observed to have an $IC_{50}$ of 0.33 ppb (i.e., 100-fold greater affinity than Cef-68).

Similar ciELISA competition curves were generated for Cef-68 and Cef-116 using a variety of cephalosporins and penicillins (not shown). The competitors can be grouped into five categories according to their chemical structures:

(1) structurally related cephalosporins containing the cephem nucleus, the thiazolyl ring, and the methoxyiminoacetamide oxime (cefotaxime, cefteram, and ceftriaxone);

(2) a cephalosporin containing the cephem nucleus, the methoxyiminoacetamide oxime, but a furan ring instead of the thiazolyl ring (cefuroxime);

(3) a cephalosporin containing the cephem nucleus, the thiazolyl ring, but a bulky oxime (ceftazidime);

(4) cephalosporins containing only the cephem nucleus as a common feature (cefaclor, cefadroxil, cefamandole, cefazolin, cefoperazone, cefoxitin, cefsulodin, cephalothin, cephapirin, and cephradine); and (5) penicillins which have the penem nucleus as a structural feature (amoxicillin, ampicillin, cloxacillin, and penicillin G).

The data from these experiments are summarized in Table I. Monoclonal anti-desCef antibodies from both Cef-68 and Cef-116 recognized all cephalosporins in category (1). However, Cef-68 has a lower relative affinity for these compounds than does Cef-116. MAb Cef-68 was observed to bind with ceftriaxone, cefteram, and cefotaxime. Likewise, MAb Cef-116 bound cefotaxime and ceftriaxone with $IC_{50}$ values comparable to those observed with ceftiofur. Binding to cefteram and cefuroxime was 10- and 100-fold reduced, respectively as compared to MAb Cef-68. No cross-reactivity was observed with any of the penicillins as shown in Table 1.

These cross-reactivity study using the ciELISA shows that certain components of the molecule (epitopes) must be present in order for antibody binding to occur. The combining sites of the MAbs reported here require the thiazolyl and methoxyiminoacetamide fragments, thus the antibodies are "recognizing" the entire 2-(2-aminothiazol-4-yl)-2-methoxyiminoacetamide fragment.

MAb Isotyping. The immunoglobulin subclass was determined using an isotype-specific ELISA kit (Fisher, Philadelphia, Pa.). The MAb produced by hybridoma Cef-68 clones was determined to be an $IgG_{2a}$ antibody with $\kappa\alpha$ light chains, and the MAb from Cef-116 was established as an $IgG_1$ antibody with kappa light chains.

Monoclonal Ascites Production. Balb/c mice were treated intraperitoneally with 0.2 mL 2,6,10,14-tetramethylpentadecane (pristane)(Aldrich Chemical Co., Milwaukee, Wis.). After a resting period of 10–14 days the mice were injected with the hybridoma cells of clone Cef-116 and ascites fluid was allowed to develop for 10 days before being collected and purified by affinity chromatography.

TABLE 1

Competitive Inhibition Values ($IC_{50}$) for Ceftiofur and Related Compounds.

| Competitors | $IC_{50}$ (ppb) Values for Antibodies[a] | |
|---|---|---|
| | Cef-68 | Cef-116 |
| Ceftiofur | 32.33 ± 0.58 | 0.33 ± 0.05 |
| Ceftriaxone | 38.67 ± 8.62 | 0.33 ± 0.05 |
| Cefotaxime | 79.67 ± 0.58 | 0.48 ± 0.05 |
| Cefteram | 200.00 ± 10.00 | 3.57 ± 0.75 |
| Cefuroxime | — | 406.67 ± 130.13 |
| Ceftizidime | — | — |
| Cephalothin | — | — |
| Cefoxitin | — | — |
| Cefazolin | — | — |
| Cefadroxil | — | — |
| Cefamandole | — | — |
| Cephradine | — | — |
| Cephapirin | — | — |
| Cefaclor | — | — |
| Cefsulodin | — | — |
| Cefoperazone | — | — |
| Ampicillin | — | — |
| Amoxicillin | — | — |
| Cloxacillin | — | — |
| Penicillin G | — | — |

[a]Results are quoted as values ± standard deviation using an average of 3–6 determinations.
—indicates that no competitive inhibition was observed at a competitor concentration of 1000 ng/well.

Example 3

The process described in Example 2 was repeated except that the immunogen was prepared from ceftiofur rather than desfuroyl ceftiofur. Ceftiofur was conjugated to BSA or OVA carrier protein via the crosslinking agents s-SMPB or s-GMBS as described in Example 1. Hybridoma cell lines were subsequently produced using these ceftiofur protein conjugates as iimmunogens using the same procedure described in Example 2.

Immunization with these ceftiofur conjugates produced monoclonal antibodies that bound the same ceftiofur protein conjugates. However, none of the monoclonal antibodies so produced exhibited the ability to bind to nonconjugated or free ceftiofur.

It is understood that the foregoing detailed description is given merely by way of illustration and that modifications and variations may be made therein without departing from the spirit and scope of the invention.

We claim:

1. A hybridoma cell line which produces and secretes monoclonal antibodies which selectively bind to ceftiofur, which is produced using an immunization preparation comprising desfuroyl ceftiofur conjugated to an immunogenic carrier through the thiol group of said desfuroyl ceftiofur.

2. The hybridoma cell line of claim 1 wherein said immunogenic carrier is a protein.

3. The hybridoma cell line of claim 1 wherein said immunization preparation further comprises a crosslinking agent between said immunogenic carrier and said thiol group of said desfuroyl ceftiofur.

4. The hybridoma cell line of claim 1, wherein said cell line is ATCC HB-12562.

5. A monoclonal antibody produced by the hybridoma cell line of claim 1.

6. A monoclonal antibody produced by the hybridoma cell line of claim 3.

7. A monoclonal antibody produced by the hybridoma cell line of claim 4.

8. A kit for the detection or quantification of the ceftiofur in a biological sample comprising a monoclonal antibody which selectively binds to ceftiofur and which is produced by the hybridoma cell line of claim 1.

9. The kit of claim 8 wherein said cell line is ATCC HB-12562.

* * * * *